United States Patent [19]

Erickson et al.

[11] Patent Number: 5,007,729
[45] Date of Patent: Apr. 16, 1991

[54] WIDE ANGLE OPHTHALMIC LENS

[75] Inventors: Phillip J. Erickson; Janet L. Crossman, both of Bellevue; Gregory L. Heacock, Seattle, all of Wash.; Martin A. Mainster, Overland Park, Kans.

[73] Assignee: Ocular Instruments, Inc., Bellevue, Wash.

[21] Appl. No.: 427,882

[22] Filed: Oct. 27, 1989

[51] Int. Cl.$^5$ .......................... A61B 3/00; G02C 7/04
[52] U.S. Cl. .................................. 351/219; 351/160 R
[58] Field of Search .................. 351/205, 219, 160 R, 351/160 H, 161, 162; 350/415, 432

[56] References Cited

U.S. PATENT DOCUMENTS

| | | |
|---|---|---|
| 3,954,329 | 5/1976 | Pomerantzeff . |
| 4,134,647 | 1/1979 | Ramos-Caldera . |
| 4,410,245 | 10/1983 | Koester . |
| 4,452,514 | 6/1984 | Spitznas . |
| 4,469,413 | 9/1984 | Shirayanagi . |
| 4,502,764 | 3/1985 | Riquin . |
| 4,627,694 | 12/1986 | Volk . |
| 4,637,699 | 1/1987 | Sigelman . |
| 4,669,839 | 6/1987 | Muchel . |
| 4,671,631 | 6/1987 | Sigelman . |
| 4,682,866 | 7/1987 | Volk . |
| 4,704,018 | 11/1987 | Takhashi . |
| 4,721,378 | 1/1988 | Volk . |
| 4,728,183 | 3/1988 | Heacock et al. . |
| 4,738,521 | 4/1988 | Volk . |

FOREIGN PATENT DOCUMENTS

| | | | |
|---|---|---|---|
| 124502 | 5/1984 | European Pat. Off. | ............ 351/219 |
| 2246182 | 3/1974 | Fed. Rep. of Germany | ...... 351/219 |
| 2660505C2 | 9/1977 | Fed. Rep. of Germany | ...... 351/219 |
| 2248814 | 5/1975 | France | .................. 351/219 |
| 2203260 | 3/1988 | United Kingdom . | |

OTHER PUBLICATIONS

P. Roussel et al., "Contact Glass for Use . . . Optical Aspects," *International Ophthalmology* 6: 183-190-(1983).

*Primary Examiner*—Rodney B. Bovernick
*Attorney, Agent, or Firm*—Christensen, O'Connor, Johnson & Kindness

[57] ABSTRACT

An ophthalmic lens which has three elements, a contact lens, a center lens, and an entry lens. The lens produces a wide field, aerial image of the fundus of the eye. The lens is particularly useful because it provides high resolution of the peripheral retina, and causes little or no distortion of the laser beam used for peripheral fundus laser treatment.

6 Claims, 1 Drawing Sheet

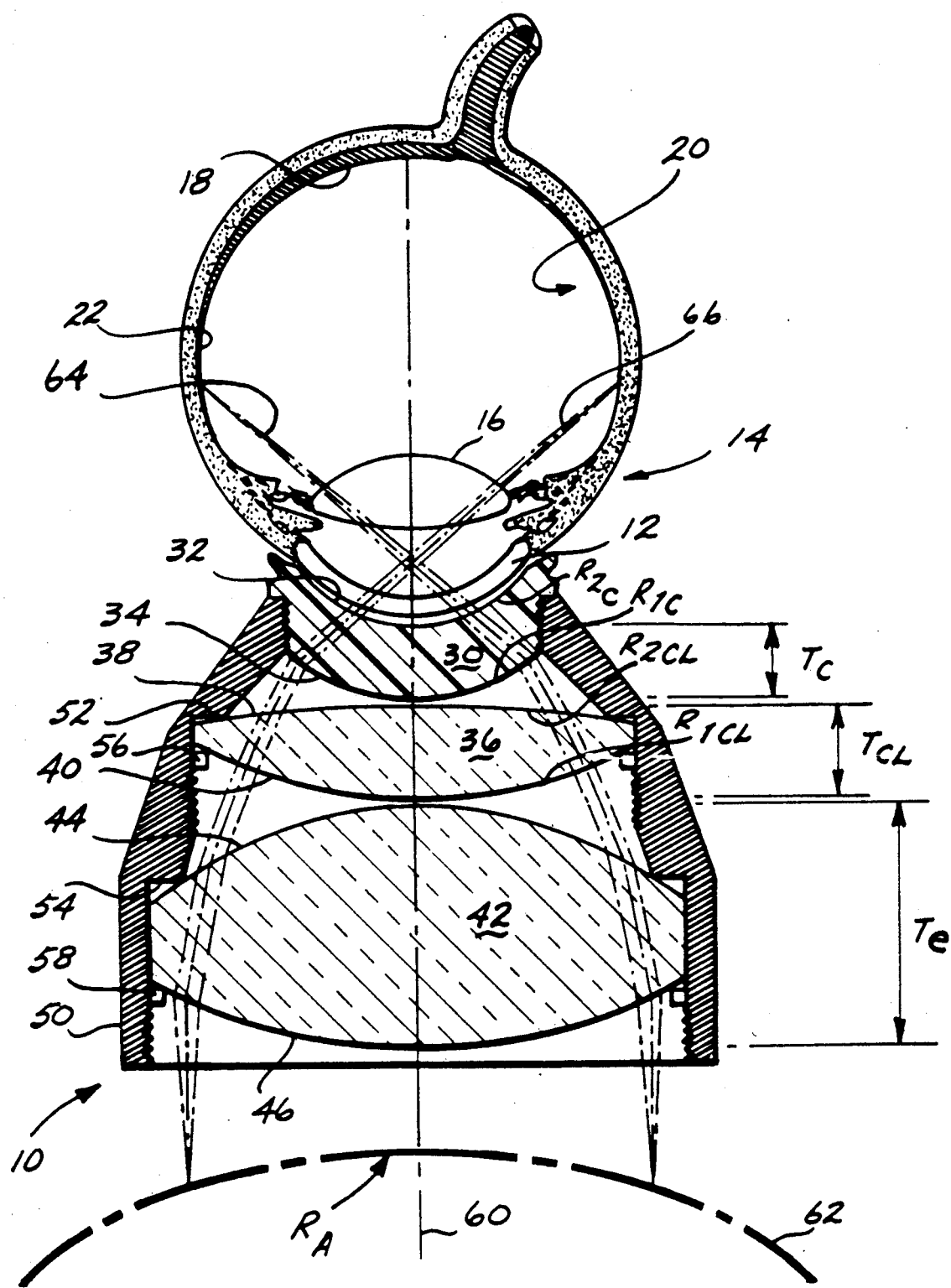

WIDE ANGLE OPHTHALMIC LENS

TECHNICAL BACKGROUND

The present invention relates to ophthalmic lenses employed in connection with ophthalmic diagnostic and surgical procedures and, more particularly, to a compound ophthalmic lens that is utilized for observation of the fundus, and particularly the peripheral retina of the eye, and for delivery of laser energy thereto.

Opthalmic lense are conventionally utilized for observation of various locations within the eye by ophthalmologists. These ophthalmic lenses normally include a contact lens, that is, a lens that directly contacts the cornea of the eye and may include an entry lens that is spaced in the anterior direction from the contact lens. The entry lens usually magnifies that portion of the eye being observed. The two lenses are normally joined by a housing. Mirrors are sometimes interposed between the contact lens and the entry lens to increase the field that can be viewed by the physicain through the lens.

Most ophthalmic lenses of the type just described have been created and designed for use as an observation tool utilized in conjunction with a slit lamp or ophthalmic microscope employed by ophthalmologists. While most prior lenses function reasonably well for use as an observation tool, the advent of laser microsurgery and the accompanying need to deliver a laser beam safely within the eye has created a need for ophthalmic lenses that not only provide improved images of the desired location in the eye but also have the capability to deliver laser energy to the desired location with minimum effect on other portions of the eye.

One example of the use of laser energy is in connection with the treatment of a patient's fundus. This treatment requires not only the capability to observe the fundus over a wide angle but the capability of being able to deliver a laser beam within the eye and focus it on the fundus. One lens currently available for wide-field fundus observation has at least three elements. Some of these elements are cemented together such that it is effectively a two lens system. The lens forms a real image within the final lens element. While the fundus image so created is adequate, axial magnification is poor, and the internal and external reflections caused by the various lens elements degrades the overall image available and reduces fundus detail if the ocular media is hazy. Moreover, the prior lens exhibits aberrations around the peripheral portion of the image and laser delivery to the peripheral retina is adversely affected by beam astigmatism induced by the lens.

A significantly improved lens is disclosed in U.S. Pat. No. 4,728,183. That lens uses an aspheric entry lens to produce an aerial image spaced from and anterior of the entry lens. The combination of the contact lens and the aspheric lens produces an aerial image that has very high resolution, even in the peripheral areas of the image. The lens also produces very little reflected or scattered light as well as a nondistorting path through which the laser beam can pass during treatment of a patient's pathology. The lens disclosed in this patent also maintains a wide cone angle on the laser beam as it passes through the patient's cornea and crystalline lens to minimize energy absorption in those elements of the patient's eye.

The lens disclosed in U.S. Pat. No. 4,728,183, however, has certain drawbacks even though it produces a superior optical image. First, the field of view is limited generally to the central and mid-peripheral fundus and, upon manipulation of the lens, to areas of the retina approaching the equator. It is desirable to increase the field of view of the lens so that the peripheral retina in the region of the equator and slightly beyond can be viewed. This increased field of view is desirable not only for delivery of laser energy for treatment of retinal detachment in the peripheral area but also for other procedures such as panretinal photocoagulation. One suggestion for increasing the field of view is to merely increase the power of the contact lens. However, the greater curvature of the anterior surface of the lens required to increase the field would greatly increase the aberrations in peripheral regions of the aerial image and thus make it unacceptable for use in diagnosis and laser delivery. Additionally, the lens disclosed in U.S. Pat. No. 4,728,183 produces an aerial image some 12 mm from the anterior surface of the entry lens. The distance between the aerial image and the patient's eye makes this lens unusable with some slit lamps employed by physicians. It is therefore desirable to reduce the distance between the aerial image and the patient's eye to provide a lens that is universally compatible with modern slit lamp microscopes.

SUMMARY OF THE INVENTION

The present invention is an improved lens that provides a wider field of view while minimizing any adverse effects upon the laser beam used to treat the peripheral retina. It also provides a lens that yields very high resolution, an image plane that appears to be relatively flat, that minimizes reflection, that is very light in weight, and that positions the image plane very close to the anterior surface of the entry lens so that it is universally compatible with modern slit lamp microscopes. The lens constructed in accordance with the present invention comprises a contact lens having a posterior surface and an anterior surface. The posterior surface has a radius of curvature compatible with the anterior surface of the cornea. The anterior surface of the contact lens has a predetermined radius of curvature $R_{1C}$. The ophthalmic lens further includes an aspheric entry lens positioned anterior to the contact lens. The surfaces of the entry lens are defined by the formula:

$$Z = \frac{CK^2}{1 + \sqrt{1 - C^2 EK^2}},$$

wherein
$C = (1/R)$,
$E = b + 1$, and
$K^2 = x^2 + y^2$, wherein for the anterior surface of the lens, R ranges from 14 mm to 50 mm and b ranges from $-54$ to $-4$, and wherein the posterior surface of said lens, R ranges from 10 mm to 25 mm and b ranges from $-0.6$ to $-2$. The ophthalmic lens further includes a center lens element positioned between the contact lens and the entry lens. The optical axes of the contact lens, the center lens and the entry lens are coincident. The center lens has a posterior surface having a radius of curvature $R_{2CL}$ and an anterior surface radius of curvature of $R_{1CL}$. The center lens element receives light rays emerging from the eye and the contact element and refracts those rays toward the optical axis of the ophthalmic lens. The entry lens collects the light rays emerging from the center lens element and produces an aerial image anterior to and in very close proximity to the entry lens. The contact lens and the center lens are positioned relative to each other and to the entry lens and have their indices of refraction and their radii of curvature chosen within certain critical limits such that the light rays originating in the peripheral retinal region of the eye are positioned within the aerial image produced by the entry lens. The indices of refraction of the contact lens can range from 1.44 to 1.97. $R_{1C}$ can range from 10.49 mm to 11.95 mm. The thickness of the contact lens can range from 0.41 mm to 7.03 mm. The indices of refraction of the center lens can range from 1.6 to 1.97. $R_{2CL}$ can range from 60.37 mm to 97.61 mm. $R_{1CL}$ can range from 18.48 mm to 29.88 mm, and the thickness of the center lens element can range from 4.29 mm to 5.29 mm.

BRIEF DESCRIPTION OF THE DRAWINGS

A better understanding of the present invention can be derived by reading the ensuing specification in conjunction with the accompanying drawing wherein the FIGURE is a schematic view of the lens constructed in accordance with the present invention shown positioned on a patient's eye.

DETAILED DESCRIPTION OF THE INVENTION

Referring first to the FIGURE, the opthalmic lens 10 constructed in accordance with the present invention is positioned over the cornea 12 of a human eye, schematically represented at 14. The eye includes the crystalline lens 16, the retina 18, and the peripheral retinal region of the eye 20 anterior to the equator 22.

The ophthalmic lens 10 includes a contact lens 30 having a posterior surface 32 and an anterior surface 34. The posterior surface of the contact lens has a radius $R_{2C}$ that is compatible with the cornea. While $R_{2C}$ could have the same radius as that of the average human cornea, it is preferred that $R_{2C}$ be slightly less than the radius of the anterior surface of the average human cornea. Preferably, the radius $R_{2C}$ is chosen so that slight vaulting occurs along the optical axis to separate the posterior surface of the contact lens from the optical region of the cornea. A preferred $R_{2C}$ is 7.45 mm. The thickness $T_C$ of the contact lens and the anterior radius $R_{1C}$ of the contact lens are chosen in accordance with the critical design parameters of the present invention discussed in more detail below.

A center lens 36 is positioned anterior to the contact lens. The posterior surface 38 of the center lens has a radius $R_{2CL}$. The anterior surface 40 of the center lens has a radius $R_{1CL}$. Both the posterior radius $R_{2CL}$ and the anterior radius $R_{1CL}$ as well as the thickness $T_{CL}$ of the center lens are also determined in accordance with the critical design parameters of the present invention, discussed in more detail below.

The entry lens 42 is an aspheric lens of the type disclosed in U.S. Pat. No. 4,728,183. Both the posterior and anterior surfaces, 44 and 46 respectively, of the aspheric lens can be defined by the formula:

$$Z = \frac{CK^2}{1 + \sqrt{1 - C^2 E K^2}},$$

wherein
$C = (1/R)$,
$E = b + 1$, and $K^2 = x^2 + y^2$,

For the anterior surface of the aspheric lens, R can range from 14 mm to 50 mm and, preferably is 19.8 mm. For the anterior surface, b can range from $-54$ to $-4$, and preferably is about $-9.7$. For the posterior surface of the lens, R can range from 10 mm to 25 mm and preferably is about 17 mm. For the posterior surface, b can range from about $-0.6$ to $-2$, and preferably is about $-0.7$. The sign convention for the foregoing formula is that $+z$ extends from the vertex of the surface in the direction of the center of the lens. The thickness $T_e$ of the aspheric lens along the optical axis can range from 8.5 mm to 16.5 mm, and is preferably 12.4 mm. A most preferred diameter for the aspheric lens is about 28 mm.

The contact lens, center lens, and aspheric entry lens can be made from any suitable optically transparent material such as polymethylmethacrylate or glass. In the preferred embodiment of the invention, the contact lens comprises polymethylmethacrylate having an index of refraction of $1.49 \pm 0.01$. In the preferred embodiment, the center lens is comprised of glass having an index of refraction of $1.81 \pm 0.01$, while the aspheric entry lens has an index of refraction of $1.52 \pm 0.01$. The three lenses are held by a lens holder 50 of conventional design. The holder positions the lenses about 0.5 mm apart. The circumference of the contact lens is externally threaded and engages an internally threaded bore at the posterior end of the cone, while the center lens and the aspheric lens rest on shoulders 52 and 54 and are retained against those shoulders by conventional retaining rings 56 and 58.

In use, light from the fundus in the region of the optical axis of the eye in the lens travels along a path indicated by light ray 60 through the crystalline lens 16, the cornea 12 and along the optical axis of the ophthalmic lens 10. The rays are focused in an aerial plane indicated by dot-dash line 62, anterior to but in close proximity to the anterior surface of the entry lens 42. In accordance with the present invention, light rays from the peripheral retinal area 18 of the eye travel along paths indicated by ray tracing 64 and 66. The rays pass through the crystalline lens 16 and the cornea 12 and into the contact lens 30. The contact lens, designed in accordance with the present invention, refracts the rays toward the optical axis of the lens. The rays are then intercepted by the peripheral portions of the center lens 36 which in turn refracts the rays again toward the optical axis of the lens. The rays 64 and 66 are then intercepted and refracted by the entry lens and focussed at the aerial image plane 62. Without the use of the center lens, an aspheric lens of a practical diameter could not be placed sufficiently close to the contact lens to intercept the rays from the peripheral retinal regions of the eye.

In accordance with the preferred embodiment of the invention, the aerial image plane is not a true plane, but is concave in the anterior direction. If the optics are designed to provide a truly planar image, an optical illusion that the central portion of the eye is closer to the observer than the peripheral portions of the eye is created. As a consequence, the optics are designed so that the peripheral portions of the aerial image 62 are closer to the observer than the portion of the aerial image lying along the optical axis. It is preferred that the aerial image be positioned greater than 2 mm, but less than 10 mm, from the anterior surface of the entry lens, and more preferably from 6.0 mm to 7.0 mm from the entry lens.

The optics of the present invention are designed to be compatible with the aspheric lens defined above. Applicants have found that the optical parameters of the contact lens and the center lens are critical to provide the desired results, that is, an ophthalmic lens that maximizes the field of view, provides a high resolution aerial image, provides an aerial image plane that appears to be relatively flat, minimizes internal reflections, insures that the aerial image plane is close to the anterior surface of the entry lens, and has a relatively overall light weight.

The lens parameters discovered by applicants are set forth in the table below. A set of values for which a workable combination of elements can be found are set forth in the preferred range of parameters. A second set of parameters are most preferred and encompass the preferred embodiment of the present invention. These parameters are for a contact lens composed of polymethylmethacrylate in combination with glass center and entry lens elements.

TABLE

|  | Preferred | Most Preferred |
|---|---|---|
| Contact Lens |  |  |
| $R_{2C}$ |  | 7.45 mm |
| $R_{1C}$ | 10.49 to 11.95 mm | 11.5 ± .2 mm |
| $T_C$ | 0.41 to 7.03 mm | 4.25 ± .2 mm |
| $N_C$ | 1.44 to 1.97 | 1.49 ± .01 |
| Center Lens |  |  |
| $R_{2CL}$ | 60.37 to 97.61 mm | 81.31 ± .2 mm |
| $R_{1CL}$ | 18.48 to 29.88 mm | 24.89 ± .2 mm |
| $T_{CL}$ | 4.29 to 5.29 mm | 4.85 ± .2 mm |
| $N_{CL}$ | 1.60 to 1.97 | 1.81 ± .01 |

Also in the preferred embodiment, the respective diameters of the lenses are 14.1±0.2 mm, 23.0±0.2 mm, and 28.0±0.2 mm. While it is desirable to position the three lenses as closely as possible to each other, some actual separation must by necessity be present. Thus it is preferred that the distances between each of the lenses is approximately 0.5 mm. These most preferred parameters provide an aerial image located about 6.3 mm from the anterior surface of the entry lens. The aerial image has a radius of curvature $R_A$ of approximately 25 mm and a diameter of about 26 mm.

A lens constructed and designed in accordance with the parameters set forth above will achieve all of the functional characteristics listed above. The present invention has been disclosed in connection with a preferred embodiment. It is intended that one of ordinary skill will be able to effect various alternations, substitutions of equivalents, and make other changes without departing from the broad concepts disclosed herein. It is therefore intended that the Letters Patent granted hereon be limited only by the definition contained in the appended claims and equivalents thereof.

The embodiments of the invention in which an exclusive property or privilege is claimed are defined as follows:

1. An ophthalmic lens for observing the fundus including the peripheral retinal regions of the eye and for delivering laser energy thereto comprising:
   a contact lens having a posterior surface and an anterior surface, said posterior surface having a radius of curvature ($R_{2C}$) compatible with the anterior surface of a cornea, the anterior surface of the contact lens having a predetermined radius of curvature $R_{1C}$,
   an entry lens positioned anterior to the contact lens, the entry lens being aspheric, the surfaces of the entry lens being defined by the formula:

$$Z = \frac{CK^2}{1 + \sqrt{1 - C^2 EK^2}},$$

wherein
   $C = (1/R)$,
   $E = b + 1$, and
   $K^2 = x^2 + y^2$,
wherein for the anterior surface of the lens, R ranges from 14 mm to 50 mm and b ranges from $-54$ to $-4$, and wherein for the posterior surface of said lens, R ranges from 10 mm to 25 mm and b ranges from $-0.6$ to $-2$, said entry lens having a thickness ranging from 8.5 mm to 16.5 mm, and
   a center lens positioned between the contact lens and the entry lens, the optical axes of the contact lens, the center lens, and the aspheric lens being substantially coincident, the center lens having a posterior surface having a radius of curvature $R_{2CL}$, the anterior surface of the entry lens having a radius of curvature $R_{1CL}$, the center lens element receiving light rays emerging from the eye and the contact lens and refracting the light rays toward the optical axis of the ophthalmic lens, the entry lens collecting the light rays emerging from the center lens and producing an aerial image anterior to and in close proximity to the entry lens, the contact lens and the center lens element being positioned relative to each other and to the entry lens and having their radii of curvature chosen such that light rays originating in the peripheral retinal region of the eye are positioned within the aerial image produced by the entry lens,
   wherein the indices of refraction of said contact lens can range from 1.44 to 1.97, $R_{1C}$ can range from 10.49 mm to 11.95 mm and the thickness of the contact lens ($T_C$) can range from 0.41 mm to 7.03 mm, and wherein the indices of refraction for the center lens can range from 1.60 to 1.97, $R_{2CL}$ can range from 60.37 mm to 97.61 mm, $R_{1CL}$ can range from 18.48 mm to 29.88 mm and the thickness of the center lens ($T_{CL}$) can range from 4.29 mm to 5.29 mm.

2. The ophthalmic lens of claim 1, wherein said aerial image is concave in the anterior direction.

3. The ophthalmic lens of claim 1, wherein the contact lens comprises polymethylmethacrylate, and the center lens and the entry lens comprise glass.

4. The ophthalmic lens of claim 3, wherein the index of refraction of the entry lens is 1.52±0.01, the index of refraction of the center lens is 1.81±0.01, $R_{1CL}$ is 24.89±0.2 mm, $R_{2CL}$ is 81.31±0.2 mm, $T_{CL}$ is 4.85±0.2 mm, and wherein the index of refraction of the contact lens is 1.49±0.01, $R_{1C}$ is 11.5±0.2 mm, $R_{2C}$ is 7.45±0.2 mm, and $T_C$ is 4.25±0.2 mm.

5. The opthalmic lens of claim 1, wherein the aerial image is positioned greater than 2 mm and less than 10 mm from the anterior surface of the entry lens.

6. The ophthalmic lens of claim 5, wherein the aerial image is positioned from 6.0 mm to 7.0 mm from the anterior surface of the entry lens.

* * * * *

UNITED STATES PATENT AND TRADEMARK OFFICE
CERTIFICATE OF CORRECTION

PATENT NO. : 5,007,729

DATED : April 16, 1991

INVENTOR(S) : P.J. Erickson et al.

It is certified that error appears in the above-identified patent and that said Letters Patent is hereby corrected as shown below:

| Column | Line | |
|---|---|---|
| 1 | 11 | "Opthalmic" should be --Ophthalmic--. |
| 1 | 11 | "lense" should be --lenses--. |
| 1 | 21 | "physicain" should be --physician--. |
| 1 | 54 | "and" should be --an--. |
| 3 | 28 | "opthalmic" should be --ophthalmic--. |
| 4 | 2 | "preferably" should be --preferably,--. |
| 4 | 51 | "focussed" should be --focused--. |
| 5 | 53 | "alternations," should be --alterations,--. |
| 6 | 26 | "anterior surface of the entry lens" should be --anterior surface of the center lens--. |
| 6 | 62 | "opthalmic" should be --ophthalmic--. |

Signed and Sealed this

Seventh Day of January, 1992

*Attest:*

HARRY F. MANBECK, JR.

*Attesting Officer*  *Commissioner of Patents and Trademarks*